US012799057B2

(12) United States Patent
Engelberth et al.

(10) Patent No.: US 12,799,057 B2
(45) Date of Patent: Nov. 17, 2026

(54) SCALABLE EXTRACTION OF LUTEIN AND ZEAXANTHIN FROM CORN PRODUCT

(71) Applicant: Purdue Research Foundation, West Lafayette, IN (US)

(72) Inventors: Abigail S. Engelberth, West Lafayette, IN (US); Emily E. Aicher, St. Charles, IL (US)

(73) Assignee: Purdue Research Foundation, West Lafayette, IN (US)

(*) Notice: Subject to any disclaimer, the term of this patent is extended or adjusted under 35 U.S.C. 154(b) by 179 days.

(21) Appl. No.: 18/626,945

(22) Filed: Apr. 4, 2024

(65) Prior Publication Data

US 2024/0336547 A1 Oct. 10, 2024

Related U.S. Application Data

(60) Provisional application No. 63/457,363, filed on Apr. 5, 2023.

(51) Int. Cl.
*C07C 29/84* (2006.01)
*A23L 19/00* (2016.01)

(52) U.S. Cl.
CPC .............. *C07C 29/84* (2013.01); *A23L 19/00* (2016.08)

(58) Field of Classification Search
CPC ... C07C 29/84; C07C 2601/16; C07C 403/24; A23L 19/00; A23L 33/105
USPC .......................................................... 585/833
See application file for complete search history.

(56) References Cited

U.S. PATENT DOCUMENTS

2004/0220432 A1* 11/2004 Crombie ............ B01D 11/0203 568/824
2016/0083766 A1* 3/2016 Englert ................ A23K 20/179 435/67
2017/0183377 A1* 6/2017 Caulfield ............... B01D 11/02

* cited by examiner

*Primary Examiner* — Prem C Singh
*Assistant Examiner* — Francis C Campanell
(74) *Attorney, Agent, or Firm* — Purdue Research Foundation

(57) ABSTRACT

The present disclosure provides for a method scalable extraction of carotenoids, such as lutein and zeaxanthin from corn products utilizing pressurized hot water extraction (PHWE) which uses high pressures and temperatures to change solvent properties of water and force unlikely extractions of desired products.

16 Claims, 5 Drawing Sheets

FIG. 2

RESULTS

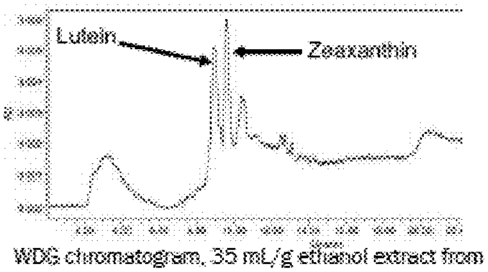

WDG chromatogram, 35 mL/g ethanol extract from Soxhlet.

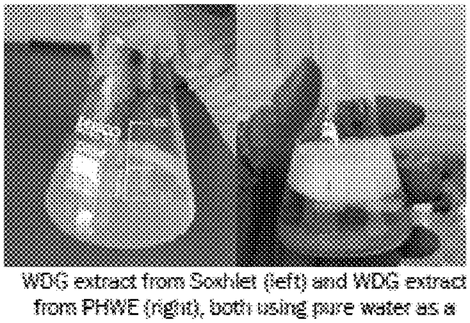

WDG extract from Soxhlet (left) and WDG extract from PHWE (right), both using pure water as a solvent.

Preliminary results are consistent with previous exploratory and previous work[2]. Ethanol appears to be the superior solvent in Soxhlet extraction.

Water extract from PHWE appears superior to water extract from Soxhlet extraction. Quantification and further work are necessary to determine if the difference in physical appearance is because of lutein and zeaxanthin or other extractives.

Initial lutein and zeaxanthin mass from Soxhlet extraction

| | Solid Loading [mL/g] | Lutein Mass [mg] | Zeaxanthin Mass [mg] |
|---|---|---|---|
| Ethanol | 35 | 0.040 | 0.027 |
| | 40 | 0.036 | 0.017 |
| Ethyl Acetate | 35 | 0.014 | 0.010 |
| | 40 | 0.009 | 0.007 |

SCALABLE EXTRACTION OF LUTEIN AND ZEAXANTHIN FROM CORN PRODUCT

CROSS-REFERENCE TO RELATED APPLICATION

This application relates to and claims the benefit of U.S. provisional application 63/457,363, filed on Apr. 5, 2023. The contents of which are expressly incorporated herein by reference in its entirety into this present disclosure.

FIELD OF INVENTION

This disclosure relates to the extraction of carotenoids, such as Lutein and Zeaxanthin from corn products. In particular, the disclosure describes methods for the extraction of useful carotenoids such as Lutein and Zeaxanthin from wet distiller's grain (WDG) and dried distiller's grains and solubles (DDGS) via a unique extraction process utilizing water as the extraction solvent that will be scalable for industrial application. The present disclosure provides for methods of Pressurized hot water extraction (PHWE) of corn products, which uses high pressures and temperatures to change the water solvent properties and force unlikely extractions. The PHWE extractions allow for lutein and zeaxanthin to be extracted into solvents and solutions that otherwise would be unfavorable at standard conditions. The increased pressure and temperature change the properties of the solvent and allow for water and water-organic solvent mixtures to extract lutein and zeaxanthin despite polarity differences. This process is the most novel part of the project because it is more likely to be operable at an industrial scale, whereas the Soxhlet extraction is limited to benchtop applications.

BACKGROUND

This section introduces aspects that may help facilitate a better understanding of the disclosure. Accordingly, these statements are to be read in this light and are not to be understood as admissions about what is or is not prior art.

Lutein and zeaxanthin are sought-after nutritional supplements. The present disclosure provides for a water-based extraction method that can be scaled. Bioethanol remains a key industry in the quest for sustainable fuels. Bioethanol, when produced from corn, also creates wet and dried distiller's grains (Wet Distiller's Grain; WDG and Dried Distiller's Grains and Solubles; DDGS), the waste byproduct of bioethanol production from corn. Distiller's grains contain non-negligible amounts of carotenoids lutein and zeaxanthin, which are common eye health supplements.

Pressurized Hot Water Extraction (PHWE) is a technique used to perform extractions of key compounds from plant matter. Mixing biomass and solvent in a pressurized vessel and submerging it in a high-temperature sand bath allows the extraction of desired compounds with solvents which would otherwise be incompatible. Use of water at a high pressure and temperature—in the sub-critical region—decreases the dielectric constant of water and allows less polar compounds to solubilize.

With the present disclosure describing the fundamental discovery of a unique process and methods for extraction from corn products, one of ordinary skill in the are would be able to use the teachings of the present disclosure to implement the disclosed process in a variety of forms. Those skilled in the art will recognize that numerous modifications can be made to the specific implementations described above. The implementations should not be limited to the particular limitations described. Other implementations may be possible.

The practice of pressurized liquid extraction, or accelerated solvent extraction, is a known art and is conventionally based on extraction at elevated temperatures (from about 50-200 C) and pressure (from about 500-3000 psi) to maintain the solvent in liquid states for a desired period of time (from about 5-10 min). It is known that extraction can be conducted from about room temperature to 200 C, and high pressure (from about 4 to 20 MPa) as the rise in temperature increases the solubility of analytes as well as mass transfer, and lowers the viscosity of the solvents.

To our knowledge, the standard technique for recovery of lutein and zeaxanthin is solvent extraction, as is used to commercially recover lutein and zeaxanthin from marigold flowers. Lutein and zeaxanthin are primarily recovered from marigold flowers and require further chemical processing to be converted into their bioavailable form for nutritional supplements.

The ability to extract lutein and zeaxanthin from corn utilizing water as the solvent, not only opens up the market for these supplements, but eliminates the need for chemical processing, as lutein and zeaxanthin from corn are already in their bioavailable form. DDGS and WDG are remnant corn from bioethanol processing and provide a convenient source of corn for lutein and zeaxanthin extraction, which can then be used in the growing market of nutritional supplements. The potential of opening the market on lutein and zeaxanthin can provide substantial additional revenue streams for corn producers and processors.

SUMMARY OF THE DISCLOSURE

The present disclosure provides for a water-based extraction method that can be scaled. The present disclosure describes solvent make-up, solids loading, and extraction times. The present disclosure provides for the manipulation of extraction pressure correlated to the desired effects based upon the described methods.

The present disclosure provides for a scalable method of lutein and zeaxanthin extraction from DDGS, wherein the DDGS is sealed within a pressure chamber, such as the InstantPot™ (https://instantpot.com/) and extracted under conditions following the pressure cook function of the apparatus.

Thus, the present disclosure provides for unexpected methods for the extraction of lutein and zeaxanthin from corn products utilizing water as the extraction solvent. The methods described demonstrate the conditions and relationship of parameters of the extraction conditions which will lead to the successful extraction of the desired products utilizing water as the solvent.

In particular, where the pressure level of the hot-water extraction process is varied, the limits for such variation are defined by the requirements of the disclosed reaction parameter function which correlates the changing dielectric constant of the water as pressure increases. Similarly, the time of extraction can be modified to enhance or control the level of extraction as the sample will have more time to interact with the solvent under pressure, and thus yield more product. However, the limitation for the exposure time is dictated by the stability of the thermally labile carotenoids.

Thus the present disclosure provides for a method of carotenoid extraction from corn products comprising the pressure hot-water extraction treatment of a sample of corn products. In one embodiment the corn product is wet distiller's grains (WDG) or dried distiller's grains and solubles (DDGS). The present disclosure also provides for the use of co-solvents, such as organic solvents in combination with the water solvent.

The present disclosure provides for a scalable method of carotenoid extraction from corn products comprising the pressure hot-water extraction treatment of a sample of corn products. In one embodiment the corn product is wet distiller's grains (WDG) or dried distiller's grains and solubles (DDGS). The parameters for scaling the reaction to larger volumes are generally described by the relationship of component parameters defined by the following equations:

$$m_{small} = \left(C_{resol}\left[\frac{\text{g}}{\text{mL}}\right] * V_{resol}[\text{mL}]\right)$$

$$\frac{m_{small}}{V_{small}} = \frac{m_{total}}{V_{total}}$$

$$m_{tot} = \frac{\left(C_{resol}\left[\frac{\text{g}}{\text{mL}}\right] * V_{resol}[\text{mL}]\right)}{V_{small}[\text{mL}]} * V_{total}[\text{mL}]$$

Thus in particular the present disclosure provides for:

1. A method for extraction of carotenoids from corn products using Pressurized Hot Water Extraction (PHWE).
2. The method as above wherein the corn product is wet distiller's grains (WDG) or dried distiller's grains and solubles (DDGS).
3. The method as above wherein the mass of starting material is varied to adjust the resulting extraction product yield.
4. The method as above wherein the volume of water is varied.
5. The method as above wherein the solvent comprises water and one or more additional suitable solvent.
6. The method as above wherein the time or extraction is varied to adjust the resulting extraction product yield.
7. The method as above wherein the pressure of the extraction vessel is adjusted to vary the resulting extraction product yield.
8. The method as above wherein the extraction product is further processed by one or more of the following methods: separation, centrifugation, foam fractionalization, resolubilization, or chromatography.
9. The method as above where the carotenoid is lutein or zeaxanthin.
10. A process for carotenoid extraction from corn products comprising the steps:
    a. preparing a sample of corn products for extraction;
    b. subjecting a sample of corn products to pressure hot-water extraction treatment in an extraction vessel;
    c. monitoring the pressure, temperature, and time components of the reaction conditions of the extraction process;
    d. collecting the extraction products;
    e. refining the extraction products to collect the carotenoids.
11. The process as above where the pressure, temperature and time components are monitored such that the dielectric constant of water changes as pressure increases which allows for greater solubilization of more hydrophobic compounds, for sufficient time to effect extraction of the carotenoids, but does not overly degrade the carotenoids that are thermally labile.
12. The process as above where the corn product is wet distiller's grains (WDG) or dried distiller's grains and solubles (DDGS).
13. The process as above where the carotenoid is lutein or zeaxanthin.
14. The process as above where one or more co-solvents other than water are used in the extraction process.
15. The process as above where the reaction products from the extraction process are refined by one or more of the following methods: separation, centrifugation, foam fractionalization, resolubilization, or chromatography.

BRIEF DESCRIPTION OF THE DRAWINGS

FIG. 2 illustrates results for extraction processes.

DETAILED DESCRIPTION

Figure 1:
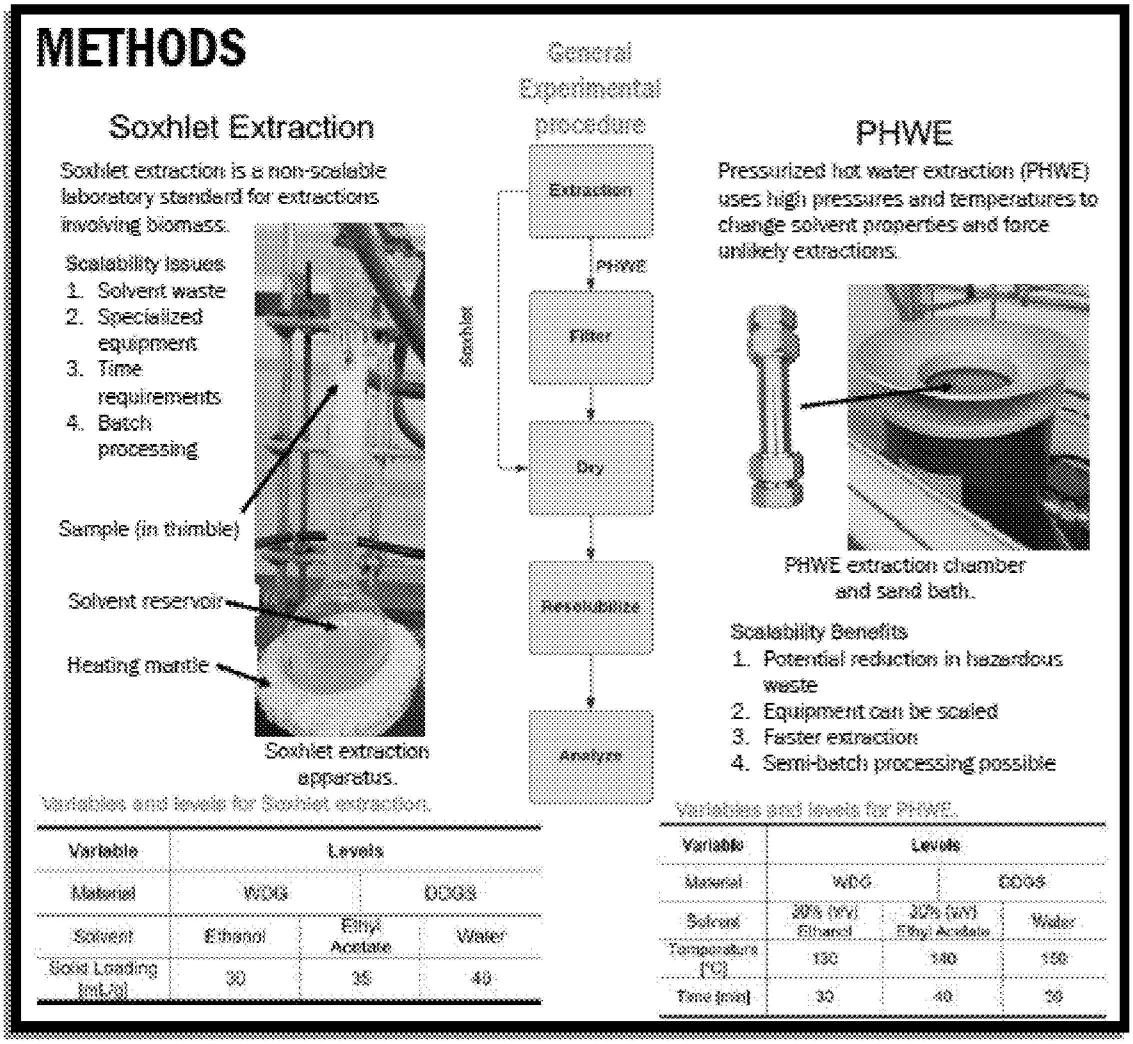
FIG. 1 illustrates aspects of the present disclosure comparing bench apparatus for Soxhlet extraction and PHWE.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

The present disclosure provides methods for use of PHWE, when used with either wet distiller's grains (WDG) or dried distiller's grains and solubles (DDGS) from corn, permits the extraction of carotenoids lutein and zeaxanthin with water. The present method can be used with other polar co-solvents or mixtures of solvents like water and ethanol or ethyl acetate. In a preferred embodiment, the solvent is about 100% water. In other embodiments, the solvent can be about an 99:1 (v/v) water to other component mixture. In further embodiments, the solvent can be from about 99:1 to about 60:40 (v/v) water/organic co-solvent mixture. The advantage of the disclosed process is the discovery that water as solvent is sufficient, and thus the minimization of the need for co-solvent.

Soxhlet Extraction is a non-scalable laboratory standard for extractions involving biomass. The present disclosure provides for methods of Pressurized hot water extraction (PHWE) which uses high pressures and temperatures to change solvent properties and force unlikely extractions.

Preliminary results with Ethanol appear to be the superior solvent in Soxhlet extraction. However, the present results demonstrate that Water extract from PHWE appears superior to water extract from Soxhlet extraction. Quantification and further work are necessary to determine if the difference in physical appearance is because of lutein and zeaxanthin or other extractives.

Soxhlet Extraction Procedure

Materials Needed

- 3 500 mL round bottom (RB) flask
- 3 Soxhlet tubes
- 4 100 mL Erlenmeyer flasks
- 1 250 mL graduated cylinder
- 2 250 mL Erlenmeyer flasks
- 2 10 mL volumetric flasks
- Boiling stones
- 200 proof ethanol
- HPLC grade ethyl acetate
- Distilled water
- 3 cellulose thimbles
- DDGS or WDG samples
- 2 culture tubes
- P1000 micropipette
- Transfer pipettes
- 0.45 um nylon filters
- 3 mL luer lock syringes
- 6 mL luer lock syringes Reference Data

TABLE 1

Masses of DDGS and WDG to use for sample measurement

| Material | Wet mass to be used (g) 30 mL/g | 35 mL/g | 40 mL/g |
|---|---|---|---|
| DDGS | 6.95 | 5.96 | 5.22 |
| WDG | 16.16 | 13.86 | 12.13 |

TABLE 2

Approximate mantle temperature settings and corresponding solvents to achieve desired reflux rate

| Solvent | Mantle 1 | Mantle 2 | Mantle 3 |
|---|---|---|---|
| Ethanol (EtOH) | 70-72 | 68-70 | 46-48 |
| Ethyl Acetate (EtAC) | 66-68 | 64-65 | 40-42 |
| Water | 87-90 | 85-87 | 54-56 |

Procedure

| Procedure | Notes |
|---|---|
| **The Day Before** | |
| 1. Clean 3 500 mL RB flasks and 4 100 mL Erlenmeyer flasks if necessary. | |
| 2. Place 3 Soxhlet tubes in 105 C. oven. If RB or Erlenmeyer flasks are wet, place them in the oven as well. Leave overnight. | |
| **Experimental set up** | |
| 1. Remove RB flasks from the oven and allow them to cool to room temperature | Label with E for ethanol, A for ethyl acetate, or W for water. |
| 2. Remove the Soxhlet tubes from the 105 C. oven and allow them to cool on an oven glove on the counter. | Make sure to keep track of which flask has which solvent. |
| 3. While cooling, measure and add DDGS or WDG to thimbles according to Table 1. Record the mass of sample. | Make sure to give the proper thimble to the proper RB flask. |
| 4. Repeat 6 and 7 for all three extraction thimbles. | Some adjustment may be necessary, especially for water. |
| 5. Use pencil to label an extraction thimble, then weigh and tare the thimble. | Start timing when the first solvent drips into the Soxhlet flask. |
| 6. Label Soxhlet flasks: water, ethanol, ethyl acetate. Add 4 boiling stones to each flask. | Be sure to shake droplets off the thimble. |
| 7. Add 190 +/− 5 mL solvent to respective RB flasks. | Two Erlenmeyer flasks are needed for ethanol and ethyl acetate each. (Label two of E, two of A). |
| 8. Add thimble to a Soxhlet tube and assemble the apparatus with the RB flask in the proper mantle according to the data table you're working on. Repeat for all thimbles and mantles 1-3. | Try to avoid the boiling stones falling into the Erlenmeyer flasks. |
| 9. Turn on cooling water by pulling both levers to the horizontal at the same time. | Label SWW [date] |
| 10. Plug in surge protector (and turn it on). Turn on heating mantles. | If Erlenmeyer flasks are not available, simply cool RB flasks, cover, and place in the fridge. |
| 11. Adjust heating mantles to proper settings according to Table 2. | |
| 12. Ethanol and ethyl acetate should siphon every 6-10 minutes, water should siphon 12-15 minutes. | |
| 13. Reflux for 4 hours. | |
| 14. After 4 hours, turn off mantles and water. When the flasks are no longer boiling, remove them from the mantles and place on cork rounds. | |

TABLE 2-continued

| Approximate mantle temperature settings and corresponding solvents to achieve desired reflux rate | |
|---|---|
| 15. Use tweezers to pull the thimble out of the Soxhlet tube. Place thimbles in a beaker under the fume hood to dry. | |
| 16. Empty contents of Soxhlet tubes into the RB flasks. | |
| 17. While flasks are cooling, label Erlenmeyer flasks (E1, E2, A1, A2). | |
| 18. Swirl each RB flask (they don't need to be completely cool, but they shouldn't be HOT). | |
| 19. Split the contents of the RB flask between the two Erlenmeyer flasks (about 95-100 mLs in each flask). | |
| 20. Rinse with a few dashes of proper solvent from a transfer pipette. Pour into the Erlenmeyer flasks. | |
| 21. Water, when cooled, is poured into the 250 mL graduated cylinder. | |
| 22. Measure the volume of the water extract. Record this value. | |
| 23. Pipette 2 mL of water extract into a labeled culture tube (SWW and date). Pipette 4 mL water extract into the second tube. Label it the same way. This solution is for storage. | |
| 24. Once cool, cover with parafilm and put in the fire-safe chemical fridge for drying later. | |
| 25. Dry extracts under nitrogen at 75 C. | |
| 26. Place dried resins in the vacuum oven for 24 hours at 42 C. | |
| 27. Let resins come to room temperature. | This may take several hours, not all of the resin may redissolve. Sonicate until the resins are at least no longer stuck to the tubes. ATTACH FILTER BEFORE POURING! E1 and E2 are poured into the same flask, A1 and A2 are poured into the same flask. |
| 28. FOR SMALL TUBE EXTRACTS<br>a. Pipette 1 mL of 50:50 methanol/ethyl acetate solution into each tube.<br>b. Mark the liquid level on each tube with a permanent marker.<br>c. Cover with parafilm and sonicate until resins are dissolved. Sonicate for an hour at a time.<br>d. Pull the plunger out of a 3 mL syringe and attach a syringe filter.<br>e. Pour the sonicated extract into the syringe.<br>f. Filter the extract into a second culture tube.<br>g. Using a micropipette, pipette filtered extract into an HPLC insert and place that into a labeled HPLC vial. | |
| 29. FOR ERLENMEYER FLASK EXTRACTS<br>h. Add 10 mL of 50:50 MeOH/Ethyl acetate solution to the flask and swirl to dissolve as much resin as possible. Pour into a clean 250 mL Erlenmeyer flask labeled with the solvent extract.<br>i. Repeat 6 times for each flask, pouring into the same 250 mL flask for a total of 120 mL for each solvent.<br>j. Use a 6 mL luer lock syringe to draw up solution. Attach filter.<br>k. Filter directly into an HPLC vial. | |
| 30. Analyze via HPLC. | |

The Soxhlet extraction procedure is known, but the inclusion of ethyl acetate investigates another potential extraction solvent not commonly used and not included in the original NREL procedure (Sluiter, A. et al., NREL/TP-510-42619). Drying under nitrogen provides a more time efficient way to process samples without using a vacuum, but still allowing for lower temperatures to be used. The use of nitrogen minimizes the oxidation of lutein and zeaxanthin in the sample. Drying small volumes also reduces the processing time and allows for the extrapolation of extractive mass from the small volume to the whole sample.

Pressurized Hot Water Extraction (PHWE)—Lab Scale

The PHWE process of the present disclosure relates the bounding parameters of the properties of the reaction components such that the PHWE procedure will yield desired extracted lutein and zeaxanthin from a sample using water as the solvent.

Lab-Scale Pressurized Hot Water Extraction (PHWE) Procedure

Materials

- DDGS/WDG
- 6 pressure tubes
- HPLC Grade ethyl acetate
- 200 proof ethanol
- DI water
- Ice bucket
- 6 125 mL vacuum flasks
- P1000 micropipette
- Transfer pipettes
- 0.45 um nylon filters
- 3 mL luer lock syringes
- Whatman 1 qualitative filter paper
- 6 Buchner funnels
- 6 100 mL graduated cylinders
- 12 culture tubes Reference Data

TABLE 1

Masses of DDGS and WDG to use for sample measurement

| Material | Wet mass to be used (g) |
|---|---|
| DDGS | 1.10 |
| WDG | 2.55 |

Procedure

| | |
|---|---|
| 1. Plug in sand bath and set temperature to 130, 140, or 150 C. Turn on air until bubbling. | For ethyl acetate, 9 mL ethyl acetate and 21 mL of water. |
| 2. Record mass of empty tube. Measure 2.55 g WDG into 3 tubes and 1.10 g DDGS into 3 tubes. Record mass added and to which tubes they belong. | |
| 3. Add 30 mL of water, ethanol mixture, or ethyl acetate mixture to tubes. 2 tubes per solvent. Record the amount added and to which tubes they belong. (2 tubes get 30 mL water, 2 get 30 mL EtOH mix, 2 get 30 mL EtAC mix). | |
| 4. Seal the tubes tightly (no more than two threads showing, for newer tubes). | |
| 5. Dust sand off of the tubes and ensure they are as dry as possible. Record the mass of the tube + solvent + sample. | |
| 6. Arrange all 6 tubes top-up in the carrying basket. | |
| 7. Use the thermocouple to measure the temperature inside the sand bath. | |
| 8. When the temperature is around the set temperature, submerge the basket in the sand, hooking the handle over the metal rod that hands above the bath. | |
| 9. Turn on the condenser trap. | |
| 10. Leave the tubes in the sand bath for the specified amount of time. | |
| 11. Unplug sand bath. Leave air on while the sand cools. | |
| 12. Using oven glove, remove basket and place into ice bucket. Cover with ice. | |
| 13. After 15 minutes/when cool, remove tubes and dry completely. Remove sand using the brush. | |
| 14. Measure the mass after extraction to check for leaks. | |
| 15. Vacuum filter the samples into 125 mL vacuum flasks in an ice bath. | Two samples may be done at a time. P[material][solvent] [date]. Such as PWW 4/4 or PDE 4/4. |
| 16. Rinse the sample with solvent (until pressure tube runs clear) into the filter to ensure all extractives are in the flask. | |
| 17. Filtration is finished when the solids on the filter no longer feel wet/when drips occur less frequently than 1 drop/10 s under vacuum. | |
| 18. Measure the total volume of each extract in a 100 mL graduated cylinder. Record. | |
| 19. Return extract to the vacuum flask. Swirl. | |
| 20. Pipette 2 mL of extract into a labeled culture tube. | |
| 21. Pipette 4 mL of extract into another culture tube for storage. | |

TABLE 1-continued

| Masses of DDGS and WDG to use for sample measurement | |
|---|---|
| 22. Dry under nitrogen at 65 C., and then for 24 hrs at 40 C. in the vacuum oven. | |
| 23. When dry, pipette 1 mL of 50:50 methanol/ethyl acetate solution into each tube. | Parafilm may tear. Cover the tube again. |
| 24. Mark the liquid level from the bottom of the meniscus on each tube with a permanent marker. | |
| 25. Cover with parafilm and sonicate until resins are dissolved. Sonicate for an hour at a time. | |
| 26. If the liquid levels of the tubes are below the initially marked level, add MeOH/Ethyl acetate solution until the meniscus is once again at the marked level. | |
| 27. Pull the plunger out of a 3 mL syringe and attach a syringe filter. | |
| 28. Pour the sonicated extract into the syringe. | |
| 29. Filter the extract into a second culture tube. | |
| 30. Using a micropipette, pipette filtered extract into an HPLC insert and place that into a labeled HPLC vial. | |

As illustrated in FIG. 1 and FIG. 2, which describe and show the variables and levels of the comparative processing of sample via Soxhlet extraction and the appearance of the extraction product of the PHWE process.

Figure 5:
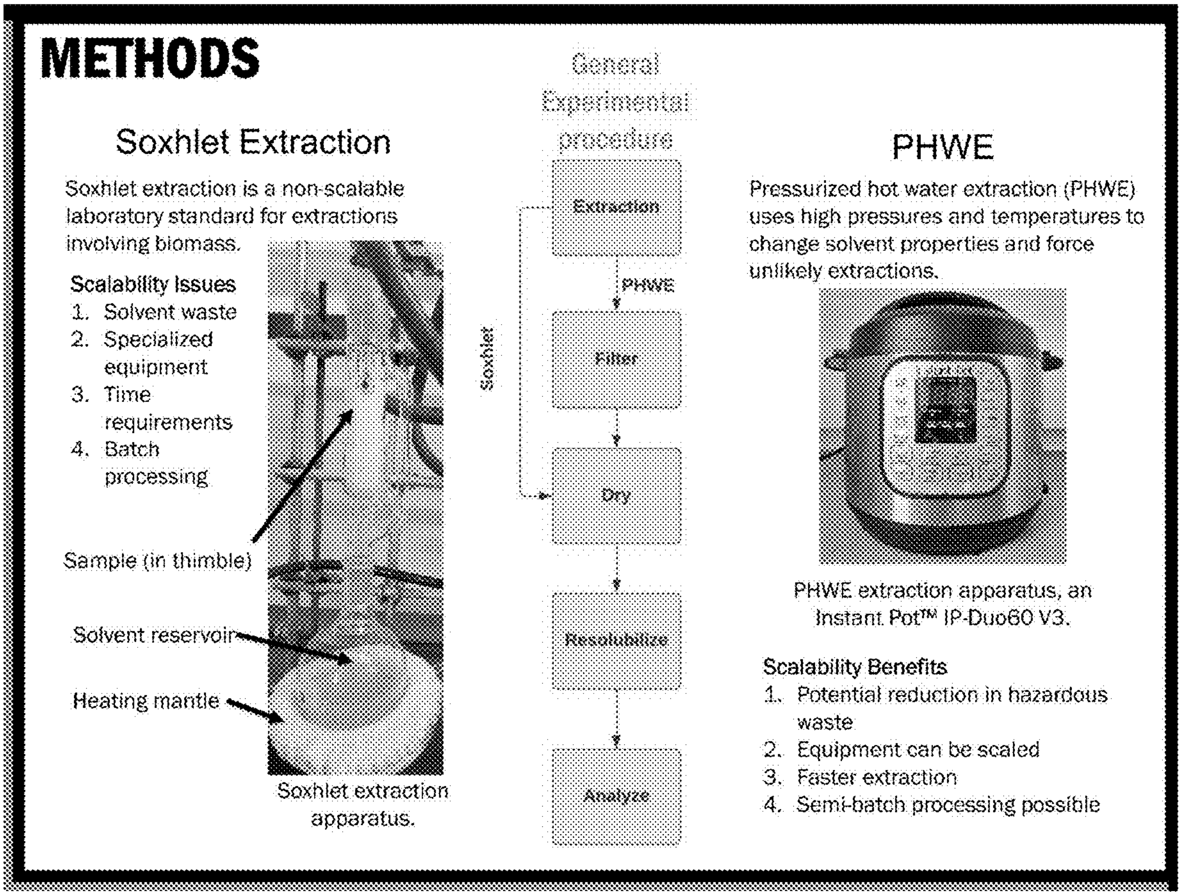
FIG. 5 Illustrates aspects of the present disclosure comparing bench apparatus for Soxhlet extraction and PHWE utilizing the pressure cooking apparatus InstantPot™.

This process can be further demonstrated utilizing a commercially available pressure-cooking vessel (model: IP-DUO60 V3 IntstantPot™) and the installed Pressure Cook function to simulate larger scale production operations under higher than atmospheric pressure and appropriate temperature. In the user manual, it is described that the IntstantPot™ operates on LOW setting at 33-55 kPa/501 psi, and at HIGH setting at 65-85 kPa/9.4-12.3 psi), and has a volume of 5.7 L/6 Quarts, and the minimum liquid for pressure cooking is 1¼ cup (375 mL/about 12 Oz.). The apparatus is illustrated in FIG. 5.

Pressurized Hot Water Extraction (PHWE)—Model System

Pressurized Hot Water Extraction (PHWE) Procedure, Instant Pot

Materials

- DDGS/WDGS
- Produce bag
- Instant Pot
- 50 mL centrifuge tubes
- Buchner funnels
- Vacuum flasks
- Whatman No. 1 and No. 4 qualitative filter paper
- Ice
- DI water
- 200 proof ethanol
- Graduated cylinders
- Nitrogen
- 50:50 Methanol/ethyl acetate
- Test tubes
- Sieves Procedure

| General Extraction Procedure | |
|---|---|
| 31. Tare Instant Pot insert with produce bag. | The current data have been collected at 10 minutes. |
| 32. Weigh desired amount of DDGS into produce bag. | The entire bulk can be characterized, but preliminary data suggests that the film that forms over the extract contains the majority of the desired analytes. |
| 33. Measure desired volume of DI water using a graduated cylinder (at least 250 mL). | |
| 34. Pour into the insert and swirl to mix. | |
| 35. Place insert inside Instant Pot and close the lid. Turn release valve to the "sealing" position. | |
| 36. Select the "Pressure Cook" function and use the "Pressure Level" button to select "High Pressure". Use the "+" and "−" buttons to set the timer to the desired extraction time. | |
| 37. After extraction is finished, the Instant Pot alarm will sound. Use a heat-resistant glove to release the pressure using the release valve. | |
| 38. Remove the insert. Remove the produce bag and squeeze to force out excess liquid. | |

-continued

| | | |
|---|---|---|
| 39. | Allow the extract to cool in the insert for approximately 1 hour. | |
| 40. | Follow respective procedure below for desired quantification. | |
| | **Film Quantification Procedure** | |
| 1. | Use a large spoon or transfer pipette to skim the top film from the insert and deposit into a centrifuge tube. | From this step forward, optimizations are being investigated. |
| 2. | Balance tubes to within 0.1 g. | |
| 3. | Centrifuge tube(s) for 10 minutes at 5,000 rpm. | |
| 4. | Add ethanol 1 mL at a time to each tube and stir until film and residue dissolve into bulk. | |
| 5. | Vacuum filter through a No. 4 filter. Rinse filter with ethanol if yellow in color. | |
| 6. | Repeat step 4 with a No. 1 filter. | |
| 7. | Record the total volume of material collected. | |
| 8. | Ensure filtrate is well-mixed and collect a 2 mL fraction of the extract. | |
| 9. | Store covered in parafilm and foil in the fridge or proceed directly to the Drying and Analysis Procedure. | |
| | **Bulk Quantification Procedure** | |
| 1. | Swirl extract and add ethanol until film layer dissolves into the bulk. | |
| 2. | Filter extract through sieves of mesh size 60, 120, 270, and 325. | |
| 3. | Pour filtered extract into centrifuge tubes and balance within 0.1 g. | |
| 4. | Centrifuge at 5,000 rpm for 10 minutes. | |
| 5. | Add ethanol 1 mL at a time to each tube and stir until film and residue dissolve into bulk. | |
| 6. | Vacuum filter through a No. 4 filter. Rinse filter with ethanol if yellow in color. | |
| 7. | Repeat step 4 with a No. 1 filter. | |
| 8. | Record the total volume of material collected. | |
| 9. | Ensure filtrate is well-mixed and collect a 2 mL fraction of the extract. | |
| 10. | Store covered in parafilm and foil in the fridge or proceed directly to the Drying and Analysis Procedure. | |
| | **Drying and Analysis Procedure** | |
| 1. | Dry extract under nitrogen at 65 C. | Parafilm may tear. Cover the tube again. |
| 2. | When dry, pipette 2 mL of 50:50 methanol/ethyl acetate solution into each tube. | |
| 3. | Mark the liquid level from the bottom of the meniscus on each tube with a permanent marker. | |
| 4. | Cover with parafilm and sonicate until resins are dissolved. Sonicate for an hour at a time. | |
| 5. | If the liquid levels of the tubes are below the initially marked level, add MeOH/Ethyl acetate solution until the meniscus is once again at the marked level. | |
| 6. | Pull the plunger out of a 3 mL syringe and attach a syringe filter. | |
| 7. | Pour the sonicated extract into the syringe. | |
| 8. | Filter the extract into a second culture tube. | |
| 9. | Using a micropipette, pipette filtered extract into an HPLC insert and place that into a labeled HPLC vial. | |
| 10. | Analyze via HPLC using established method. | |

Process Phases

Figure 3:
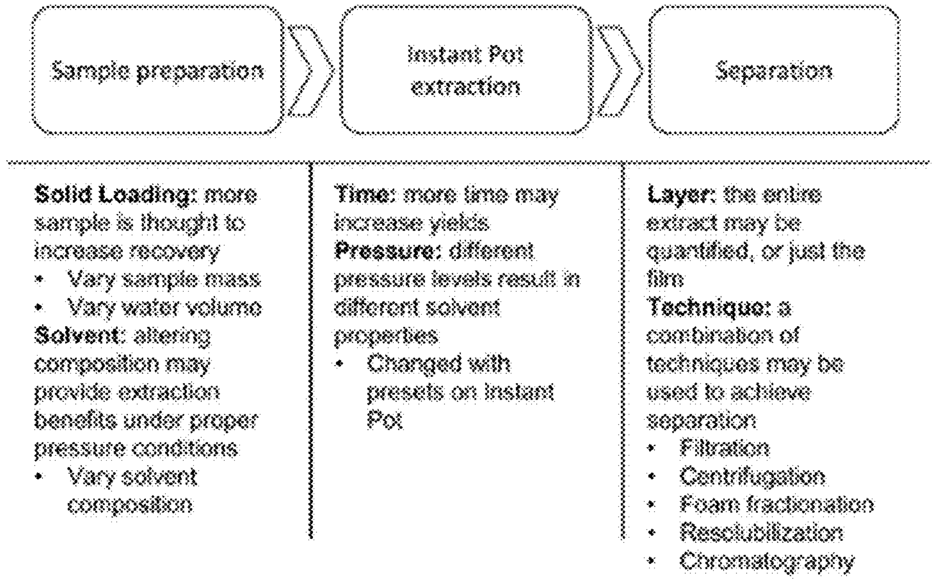
FIG. 3 Illustrates methods of the disclosure providing a summary of key processing phases and notable parameters/operations.

The overall extraction process can be described generally in the following steps:

sample preparation, extraction, and separation. Each processing phase has its own considerations and parameters that can be varied to investigate efficacy. Sample preparation and extraction parameters directly affect yield from the extraction, while sample separation parameters affect the purity of lutein and zeaxanthin recoverable from the extraction. The processing phases are illustrated and described in FIG. 3.

Sample Preparation

DDGS is prepared for extraction. Dried grains are measured and the solvent is added.

The levels of mass and volume can be adjusted, reflecting changes in the solid loading of the system. Solid loading is a measure of mass to volume and describes how concentrated the sample is in relation to the solvent used. It is suspected based on previous lab-scale work that increasing the solid loading (increasing the mass of sample for the same volume) increases the concentration of carotenoids in the extract. The solvent composition may be adjusted. The current technology focuses on the use of water alone as the extraction solvent. The addition of co-solvents may increase yield if pressure increases, this study will be possible with acquisition of a more precise reactor to study temperature/pressure effect. Suitable co-solvents include alcohols or acetates, however it is expected that ethanol and ethyl acetate would be most preferred as to their use in the Soxhlet process and relatedness to use in corn-ethanol production.

Extraction

The DDGS is sealed within the InstantPot™ and extracted under the Pressure Cook function. In this phase, the set pressure level may be modified-within very defined limits-along with the extraction time. The dielectric constant of water changes as pressure increases, which allows for greater solubilization of more hydrophobic compounds. A greater pressure (below the sub-critical point) is suspected to provide enhanced extraction conditions. Similarly, the residence time for extraction conditions is suspected to increase yield since the sample and solvent have more time to interact under pressure. Increases may be seen only to a point, however, as carotenoids are thermally labile and may degrade if left exposed to high temperatures and pressures for too long. More investigation will validate this hypothesis.

Separation

The lutein and zeaxanthin are separated from the extraction solution. The entire bulk of the extract may be tested, or just the top layer, which forms a film when cooled. Centrifugation and filtration are two operations currently applied to remove solids and concentrate lutein and zeaxanthin. Foam fractionation is being investigated as a gentle separations technique to purify the carotenoids from the water extract.

Resolubilization, Resuspension, Analysis

Figure 4:
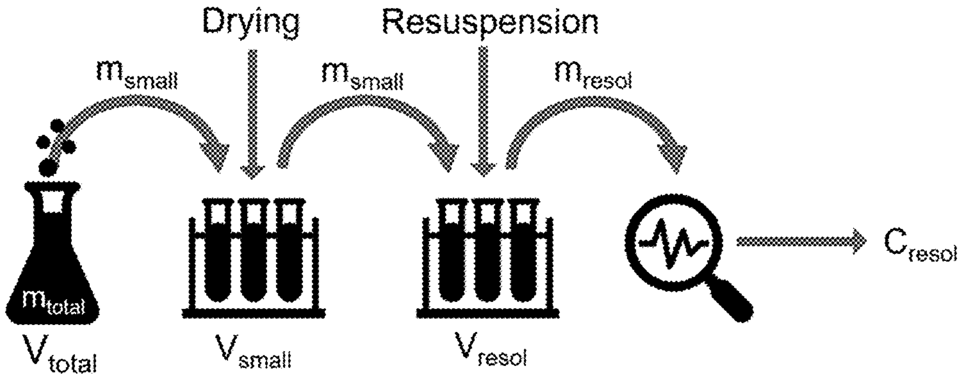
FIG. 4 Illustrates a visual representation of the resuspension (resolubilization) and analysis process for extraction products.

As illustrated in FIG. 4, a visual representation of the resuspension (resolubilization) and analysis process. In step 1, a small fraction is taken from the total extract volume. This small fraction is dried down in step 2 and resuspended in another volume in step 3 to concentrate it for analysis.

Results and Discussion

The PHWE extractions allow for lutein and zeaxanthin to be extracted into solvents and solutions that otherwise would be unfavorable at standard conditions. The increased pressure and temperature change the properties of the solvent and allow for water and water-organic solvent mixtures to extract lutein and zeaxanthin despite polarity differences. This process is the most novel part of the project because it is more likely to be operable at an industrial scale, whereas the Soxhlet extraction is limited to benchtop applications.

Current results implicate that water is a promising extraction solvent under pressure and at high temperature. When a robust pressure regulation system is in place (such as that provided by an InstantPot™), water can successfully extract lutein and zeaxanthin from DDGS.

Preliminary extractions have revealed that:

InstantPot™ water extractions yield concentrations of lutein and zeaxanthin similar to other lab-scale extraction methods.

Increasing solid loading results in higher carotenoid concentrations in extract.

Using volatile cosolvents does not appear to optimize yield in this system.

The film formed as extract cools contains the majority of the carotenoids recovered.

More investigation will explore extraction parameters and further extraction and recovery process. Fine tuning the effect of pressure and temperature interactions during extraction will enable design of robust larger-scale extraction process. Further exploration of foam fractionation of lutein and zeaxanthin from the water extract will result in a gentle yet effective purification technique.

The following equation is used to convert the results of the analytical technique, high-performance liquid chromatography (HPLC), to a reportable mass. HPLC reports lutein and zeaxanthin content in terms of concentration in mg/mL, of a small sample volume. To report the estimated total carotenoid recovery, the concentration must be converted to mass in the total extracted volume. For pressure samples, only a fraction of the volume was quantified, leading to a need to scale measured quantities in analysis to estimated quantities in the total extract.

The following equations reflect the mathematical process for both the pressure cooking and the Soxhlet procedures, described with their respective procedural steps. Below, you will find a diagram that details the experimental process visually (FIG. 4).

$$m_{small} = \left(C_{resol}\left[\frac{\text{g}}{\text{mL}}\right] * V_{resol}[\text{mL}]\right)$$

$$\frac{m_{small}}{V_{small}} = \frac{m_{total}}{V_{total}}$$

$$m_{tot} = \frac{\left(C_{resol}\left[\frac{\text{g}}{\text{mL}}\right] * V_{resol}[\text{mL}]\right)}{V_{small}[\text{mL}]} * V_{total}[\text{mL}]$$

TABLE 1

Variables with descriptions, to be used as reference for equations.

| Variable | Description | Unit |
|---|---|---|
| $C_{resol}$ | Carotenoid concentration in the resolubilized sample | [mg/mL] |
| $m_{resol}$ | Mass of carotenoid in resolubilized sample | [mg] |
| $m_{small}$ | Mass of carotenoid in small fraction of extract | [mg] |
| $m_{total}$ | Total mass of carotenoid in the entire extracted volume | [mg] |

TABLE 1-continued

| Variable | Description | Unit |
|---|---|---|
| Variables with descriptions, to be used as reference for equations. | | |
| $V_{resol}$ | Volume added to dried resin to resuspend/resolubilize carotenoids | [mL] |
| $V_{small}$ | Volume of fraction taken from the total extract | [mL] |
| $V_{total}$ | Total volume of extract | [mL] |

The first step is to convert the concentration measured from HPLC to the mass of carotenoids in the resuspended volume (step 3 above). Essentially, one must work backwards from the concentration, to the resuspension, to the small fraction, and finally to the total volume. Equation 1 calculates the mass of a carotenoid in the resuspended volume (mresol, mg). Cresol is the concentration of the carotenoid outputted by the HPLC in mg/mL, and Vresol is the volume of the resuspension.

$$m_{resol} = (C_{resol} * V_{resol}) \tag{1}$$

Using the knowledge in Equation 2 that the mass has not significantly changed in the drying step, the mass of carotenoids in Vsmall is the same as the mass in Vresol. All that changes between drying and resuspension is the amount of liquid in the sample. The mass of carotenoids is not expected to make a measurable change. Therefore, Equation 3 is made by combining Equations 1 and 2. Equation 3 is the equation reported previously.

$$m_{small} = m_{resol} \tag{2}$$

$$m_{small} = C_{resol} * V_{resol} \tag{3}$$

The next step is to scale the mass of carotenoids in the small volume (Vsmall, mL) to the total extract volume (Vtotal, mL). Scaling is accomplished by assuming the concentration in the small sample of extract is the same in the total extract; that is, the sample is well-mixed and essentially homogenous. With this assumption, Equation 4 is produced, equating the concentration in the small volume to the total volume. Solving for mtotal, the total mass of carotenoid in the entire extracted sample, Equation 5 is produced.

$$\frac{m_{small}}{V_{small}} = \frac{m_{total}}{V_{total}} \tag{4}$$

$$m_{total} = \frac{m_{small}}{V_{small}} * V_{total} \tag{5}$$

To create a one-step equation to convert from the measured value Cresol to mtotal, Equation 6 can be used. Equation 6 substitutes Equation 3 into Equation 5, creating the final version of the equation originally presented.

$$m_{total} = \frac{(C_{resol} * V_{resol})}{V_{small}} * V_{total} \tag{6}$$

The math presented here is very exclusive to the procedure used and is subject to change as new knowledge and analysis is developed, but this general though process is applied to pressure-extracted samples. A similar process is applied to Soxhlet samples as well, but is simplified since the entire Soxhlet extract is dried and quantified instead of just a small fraction (with the exception of water extracts).

Sample Calculation

Below is a sample calculation using data from Instant-Pot™ extractions with water for lutein. Note that in this example, Vresol and Vsmall are the same quantity. The small fraction taken may be resolubilized in an equivalent volume, and simplifying Equation 6 above allows for total mass to be directly solved for as the product of Cresol and Vtotal since no concentrating step is present or required. It may be noticed when using the extended equation method as well as Equation 6 that the volumes will cancel out, resulting in Equation 7. All other equations in this section correspond to their respective symbolic equations above.

Given:

$$C_{resol} = 2.309 * 10^{-4}\frac{\text{mg}}{\text{mL}}\text{lutein}$$

$$V_{resol} = 2 \text{ mL}$$

$$V_{small} = 2 \text{ mL}$$

$$V_{total} = 541 \text{ mL}$$

To Solve Using the Extended Method:

$$m_{resol} = \left(2.309 * 10^{-4}\frac{\text{mg}}{\text{mL}}\right) * (2 \text{ mL}) = 4.618 * 10^{-4}\text{mg} \tag{1}$$

$$m_{small} = m_{resol} = 4.618 * 10^{-4}\text{mg} \tag{2}$$

$$m_{total} = \frac{4.618 * 10^{-4}\text{mg}}{2 \text{ mL}} * 541 \text{ mL} = 0.125 \text{ mg lutein} \tag{3}$$

To Solve Directly Using Equation 6:

$$m_{total} = \frac{\left(\left(2.309 * 10^{-4}\frac{\text{mg}}{\text{mL}}\right) * (2 \text{ mL})\right)}{2 \text{ mL}} * 541 \text{ mL} = 0.125 \text{ mg lutein} \tag{6}$$

Simplified Equation 6, when $V_{small}=V_{resol}$:

$$m_{total} = C_{resol} * V_{total} \tag{7}$$

$$m_{total} = \left(2.309 * 10^{-4}\frac{\text{mg}}{\text{mL}}\right) * (541 \text{ mL}) = 0.125 \text{ mg lutein}$$

While the embodiments have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope.

REFERENCES

[1] Li, J., Engelberth, A. S. Quantification and purification of lutein and zeaxanthin recovered from distillers dried grains with solubles (DDGS). Bioresour. Bioprocess. 5, 32 (2018). https://doi.org/10.1186/s40643-018-0219-3

[2] Li, J. (2015). Adding Value to Bioethanol Production: Quantification and purification of lutein and zeaxanthin recovered from DDGS. [Master's thesis, Purdue University https://docs.lib.purdue.edu/dissertations/AAI1603066/] [3]

[3] InstantPot™ User Manual (from www.instapot.com)

[4] Sluiter, A. et al. Determination of Extractives in Biomass, Technical Report, National Renewable Energy Laboratory (Issue Date Jul. 15, 2005); NREL/TP-510-42619 January 2008.

We claim:

1. A method for extraction of carotenoids from a corn product comprising:

subjecting wet distiller's grains (WDG) or dried distiller's grains (DDGS) to pressurized hot water extraction, wherein water is maintained in a liquid state at a temperature above its atmospheric boiling point and below its critical point by application of pressure sufficient to prevent vaporization;

collecting an aqueous extract produced by the pressurized hot water extraction;

cooling the aqueous extract to form a surface film comprising carotenoids;

separating the surface film from a remaining aqueous phase;

and recovering carotenoids from the separated surface film.

2. The method of claim 1, wherein the surface film contains a greater concentration of lutein and/or zeaxanthin than the remaining aqueous phase.

3. The method of claim 1, wherein the surface film is collected by skimming the surface of the cooled extract.

4. The method of claim 1, further comprising centrifuging the separated surface film prior to carotenoid recovery.

5. The method of claim 4, further comprising dissolving the surface film in ethanol prior to filtration.

6. The method of claim 5, wherein the dissolved film material is filtered to remove particulate matter prior to carotenoid analysis or purification.

7. The method of claim 1 wherein the pressurized hot water extraction is conducted using water as the sole extraction solvent.

8. The method of claim 1 wherein the pressurized hot water extraction is performed in a sealed pressure vessel, wherein extraction is conducted at a temperature between about 130 °C and about 150 °C.

9. The method of claim 1, wherein extraction is conducted for about 30 minutes to about 50 minutes.

10. A process for recovery of carotenoids from a corn product comprising:

(a) contacting wet distiller's grains (WDG) or dried distiller's grains (DDGS) with water in a sealed pressure vessel;

(b) heating the water under pressure while maintaining the water in a liquid state;

(c) obtaining an aqueous extract comprising carotenoids;

(d) cooling the aqueous extract to generate a carotenoid-containing surface film;

(e) separating the surface film from the aqueous extract; and (f) recovering carotenoids from the separated surface film.

11. The process of claim 10, wherein cooling the aqueous extract produces a surface film containing a greater concentration of lutein and/or zeaxanthin than the remaining aqueous phase, and wherein the surface film is separated from a remaining aqueous phase prior to recovery of the lutein and/or zeaxanthin.

12. The process of claim 10, wherein the corn product is wet distiller's grains (WDG) or dried distiller's grains and solubles (DDGS).

13. The process of claim 11, wherein the carotenoids comprise lutein, zeaxanthin, or a combination thereof.

14. The process of claim 11, wherein the pressurized hot water extraction is conducted using water as the primary extraction solvent and the separated surface film is recovered for subsequent carotenoid purification.

15. The process of claim 11, wherein the separated surface film is further processed by one or more centrifugation, filtration, resolubilization, chromatographic separation, or a combination thereof to recover or enrich carotenoid fractions.

16. The process of claim 11, wherein the surface film is collected by skimming the surface of the cooled extract.

* * * * *